United States Patent [19]

Bourguet et al.

[11] Patent Number: 4,860,582
[45] Date of Patent: Aug. 29, 1989

[54] METHOD AND DEVICE FOR ASSESSING THE CLOGGING RISKS OF A WELL OR BORE HOLE PASSING THROUGH A POROUS REVERVOIR, MORE PARTICULARLY A GEOLOGICAL FORMATION

[75] Inventors: Lucien Bourguet, Boulogne-Billancourt; Claude Gatellier, Boulogne, both of France

[73] Assignee: Institut Francais du Petrole, France

[21] Appl. No.: 943,436

[22] Filed: Dec. 19, 1986

[30] Foreign Application Priority Data

Dec. 26, 1985 [FR] France ................... 85 19374

[51] Int. Cl.$^4$ .............................. E21B 49/02
[52] U.S. Cl. ..................................... 73/155
[58] Field of Search ................... 73/38, 153, 61.2

[56] References Cited

U.S. PATENT DOCUMENTS 3,018,660  1/1962  Schmid .................. 73/38 X

Primary Examiner—Jerry W. Myracle
Attorney, Agent, or Firm—Antonelli, Terry & Wands

[57] ABSTRACT

A method and device are provided for assessing the clogging risks of a well or bore hole into which a fluid is injected or pumped. According to this method controlled amounts of said fluid are caused to flow through a plurality of samples representative of the porous reservoir which are fed in parallel and whose temperature is maintained substantially constant, and the loss of permeability of said samples is measured as a function of time.

5 Claims, 30 Drawing Sheets

METHOD AND DEVICE FOR ASSESSING THE CLOGGING RISKS OF A WELL OR BORE HOLE PASSING THROUGH A POROUS REVERVOIR, MORE PARTICULARLY A GEOLOGICAL FORMATION

BACKGROUND OF THE INVENTION

The present invention relates to a method and device for assessing the clogging risks of a well or bore hole passing through a porous reservoir, more particularly a geological formation fed by a water bearing nappe and for determining in advance the characteristics to be given to production works, wells or bore holes, for avoiding clogging thereof.

These characteristics will for example be the diameter of the main well and its liner, the lined height, the position and characteristics of the radiating drains, the pumping rate and the lowering height of the ground water.

A first application of the invention resides in a diagnosis of the life span of worked bore holes and wells and of the working methods and procedures likely to extend it.

A second application of the invention resides in the proposal of curative or corrective treatment for a reservoir or work which risks being clogged.

Clogging phenomena affect numerous wells or bore holes passing through geological formations, particularly granular geological formations.

These phenomena reduce the working life of these works sometimes to a few years; whereas their financial amortizement is generally calculated for a twenty year period.

The financial repercussion of clogging is so great that efforts have been made for numerous years to discover means for reducing the amount of clogging when it affects the works. This search for curative means has not yet had notable success for it is often too late to act efficiently. This is why it is desirable to be capable of foreseeing beforehand the risks of clogging of a reservoir by an overall knowledge of its properties and of the evolution thereof as a function of the fluid flow in the reservoir, for example a water bearing nappe. The properties, the overall knowledge of which is important, are not limited to the properties alone of the fluid which occupies the reservoir. The clogging index is known from the fouling of a cellulose acetate membrane with a porosity of 0.45 after 15 minutes of filtration by water taken from an aquifer. Now this index does not take into account the geological formation which experimentation has not been able to reveal. The absence of the porous medium in this determination means that the physiochemistry of the interfacial phenomena cannot be correctly simulated, just as the development of microorganisms in the pores and small channels of the medium cannot be reproduced.

By way of prevention, it is advisable to determine the flow speed of the fluid during pumping or injection, which should not be exceeded so as to avoid clogging. The method of the invention allows this determination to be made on the site itself by feeding a physical model formed of several test specimens through which the fluid is caused to percolate at different speeds.

SUMMARY OF THE INVENTION

More particularly, the invention provides a method for assessing the clogging risks of a well or bore hole passing through a porous reservoir, more particularly a geological formation, into which a fluid is to be injected or pumped, wherein controlled amounts of said fluid are caused to flow through a plurality of samples representative of the porous reservoir which are fed in parallel and whose temperature is maintained substantially constant, and the loss of permeability of said samples is measured as a function of time.

In a particular embodiment, the fluid is caused to flow at different speeds through the samples fed in parallel.

It will be advantageous to provide controlled pressure differences between the inlet and outlet of each of the parallel fed samples.

The porous medium of the samples may be formed by compacted sand of known grain size distribution or else by a core sample taken from the worked reservoir.

According to a particular embodiment, the physical model, the object of the invention, is formed of several identical test tubes made from stainless steel inside which are placed core samples taken in the direction of the natural flow of the aquifer and which are fed with water taken from the aquifer itself by a pump.

It is important according to the invention to use several test tubes subjected to different flow conditions.

The invention also provides a device wherein, at least one sample representative of the porous reservoir is positioned in a sample holder through which the fluid concerned by the planned pumping or injection operation is caused to flow.

The invention provides more particularly a device for assessing the clogging risks of a well or bore hole passing through a formation, particularly a geological formation through which is a fluid flows, comprising a plurality of test tubes adapted for containing samples representative of the formation, means for maintaining the whole of said test tubes substantially at the same temperature, means for supplying these test tubes in parallel with controlled flows of said fluid and means for following the evolution of the permeability of the different samples as a function of time.

According to a particular embodiment, in the device at least one of said test tubes is in the form of a sample holder comprising a sealed flexible sheath closed at both ends and allowing the sample to be placed under the same pressure conditions which reign in its natural bed.

BRIEF DESCRIPTION OF THE DRAWINGS

Examples of embodiments of the invention are described hereafter with reference to the accompanying drawings in which.

DESCRIPTION OF THE PREFERRED EMBODIMENTS

Figure 1:
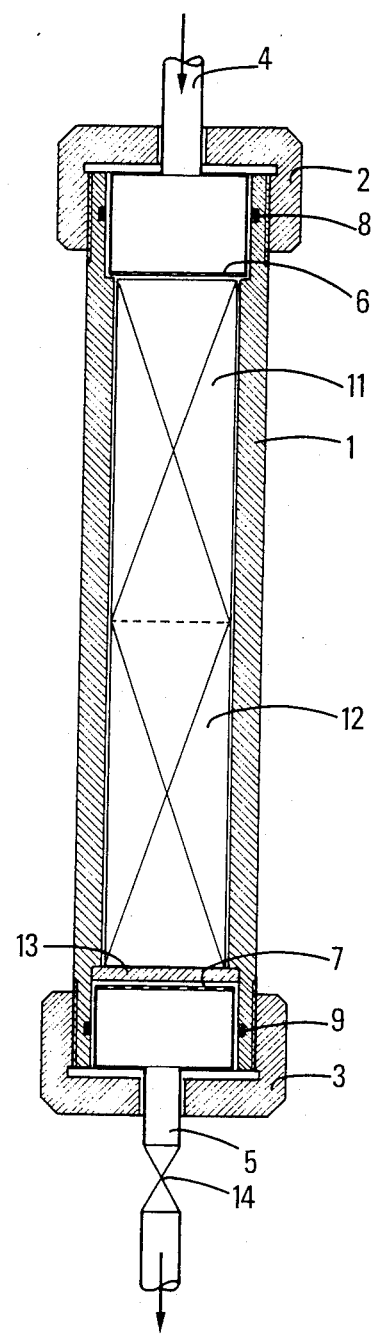
FIG. 1 shows a type of test tube or sample holder which may be used.

FIG. 1 shows by way of example one embodiment of a test tube adapted for containing samples of the porous reservoir studied, an aquifer reservoir for example.

This test tube includes a tube 1 which may for example be made from stainless steel.

At the ends of this tube may be screwed caps 2 and 3 which have orifices for the passage of inlet 4 and outlet 5 ducts, respectively, through which the fluid flowing through the sample may flow.

The ends of ducts 4 and 5 have widened sections for receiving perforated plates 6 and 7. O seals 8 and 9 provide sealing in contact with the internal wall of tube 1.

Figure 2:
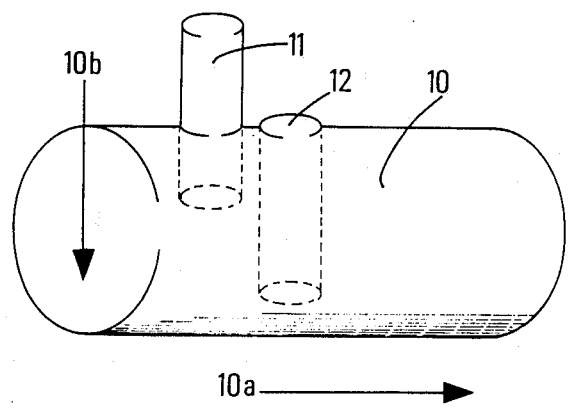
FIG. 2 illustrates one method of taking samples from the porous reservoir to be studied.

According to the embodiment of the invention illustrated in FIGS. 1 and 2, two samples of the formation to be studied are taken from a core sample 10 removed from the formation.

These samples are taken from the geological formation by means of two corer 11 and 12 (FIG. 2) which are adapted to be housed one after and below the other inside tube 1, so that the fluid introduced through duct 4 flows therethrough in series. A porous material disk 13 may if required be interposed between the corer tube 12 and the perforated plate 7. In FIG. 2, arrow 10a indicates the direction of coring in the formation. Arrow 10b indicates the flow direction of the fluid in the geological formation.

In the output duct 5 is disposed a valve 14 for adjusting the rate of the flow through the samples of the formation studied. It would of course be possible to dispose a single corer tube, or more than two corer tube in series in tube 1.

It would also be possible to dispose in tube 1 several corer tubes taken from different sides of the same porous reservoir. By different sides is here means positions at different distances from the pumping or injection point.

Figure 3:
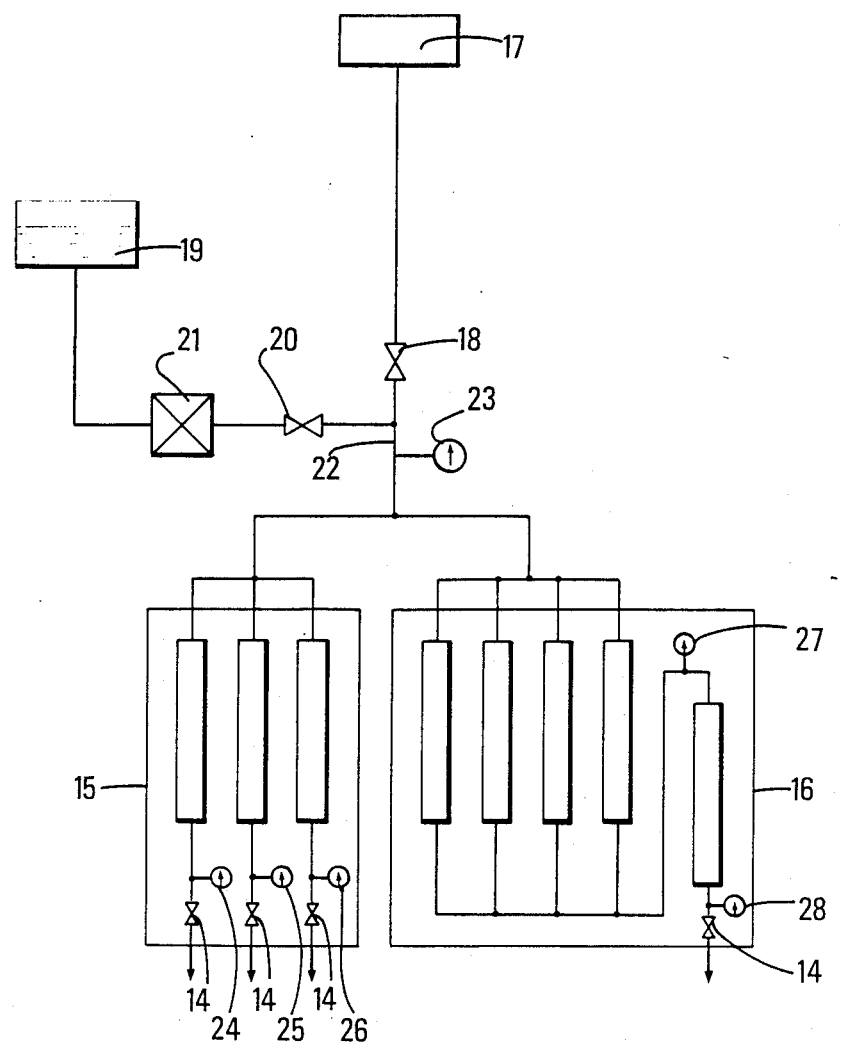
FIG. 3 shows schematically a device of the invention.

FIG. 3 shows schematically a device of the invention in which a plurality of test tubes such as those illustrated in FIG. 1 are placed in thermostatic enclosures 15 and 16 (the construction of such enclosures is within the scope of specialists and will therefore not be described here in detail). The enclosures which may be in any number may for example contain a liquid bath in which is placed an agitator driven continuously or periodically by an electric motor, the temperature of this bath being kept substantially constant by a heating resistance whose electric supply is controlled by a detector detecting the temperature of the bath.

The different test tubes may be fed in parallel from a source 17 with flow rates controlled by valves 14.

The supply by source 17 coming from the aquifer for example may be cut off by a valve 18 so as to leave room for a supply by another source 19 isolated from the circuit by a valve 20 an a microporous filter 21.

The variations of permeability of the samples as a function of time may be followed, for example, by using the device shown schematically in FIG. 3 which includes the tank 19 containing a reference fluid placed at a sufficient level above the test tubes to exert a hydrostatic load. The test tubes are then supplied with a sterile fluid from source 19, reservoir or circuit, the fluid being sterilized by the microporous filter 21, the flow being then controlled in pipe 22 by valve 20, valve 18 being closed.

The variations of permeability of the samples may also be followed by measuring the upstream and downstream pressures by means of manometric tappings 23, 24, 25, 26, 27 and 28 which may be designed for operating either at absolute pressure, or by relative measurements.

Figure 4:
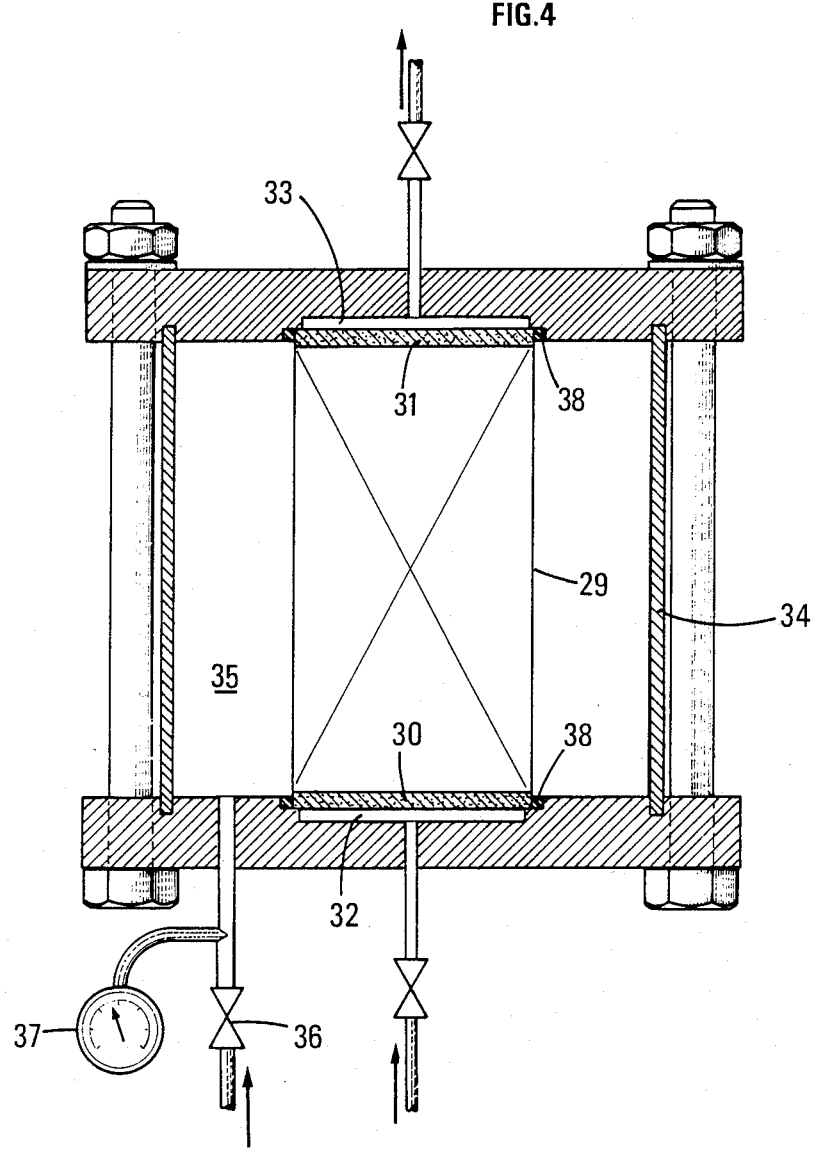
FIG. 4 shows an advantageous method of constructing a sample holder reproducing substantially the bottom pressure conditions.

FIG. 4 shows an advantageous embodiment of a sample holder reproducing substantially the pressure conditions of the porous medium.

This sample holder includes a flexible sealed sheath 29 closed at both ends by two caps 30, 31 having orifices 32, 33 for passage of the fluid.

The sample holder is immersed in an enclosure 34 containing a fluid 35 kept by a valve 36 at an adjustable pressure P controlled by a pressure gauge 37. Enclosure 34 is equipped with packers 38 for isolating from the pressure and fluid 35 the passage of the ducts connected to orifices 32, 33.

Such sample holders may be used instead of one at least of the tube tubes of FIG. 3.

With the device shown in FIG. 4, if desired, the sample studied may be subjected to an external counterpressure calculated for reconstituting the pressure conditions to which it is subjected to its natural bed: the liquid 35 contained in enclosure 34 bathes the sealed flexible sheath 29 which surrounds the sample and communicates thereto the counterpressure controlled by the pressure gauge 37 and valve 36. This counterpressure is usually separate from the pressure required for causing the fluid to flow through the orifices 32, 33 within the sampled studied.

The method of the invention is particularly applicable to the diagnosis of the lifespan of working bore holes or wells.

It is also applicable to the determination of the limit conditions of fluid flow speed and, consequently, of the optimum working conditions (flow rate, diameter of the work, dimension of the liners) to be adopted for avoiding or delaying the clogging of the planned work.

The invention is also applicable for providing, by way of correction, a change in a method of working a reservoir which risks being clogged.

What is claimed is:

1. A method for assessing the clogging risks of a well or bore hole passing through a porous reservoir, particularly a geological formation, into which a fluid is to be injected or pumped, which comprises obtaining a plurality of samples representative of the material forming the porous reservoir; placing the samples in containers arranged in parallel; maintaining the temperature of the samples within the containers substantially constant; causing controlled amounts of said fluid to flow through the plurality of samples within the containers in parallel; and measuring the loss of permeability of said samples as a function of time.

2. The method as claimed in claim 1, wherein said fluid is caused to flow at different speeds through said samples fed in parallel.

3. The method of claim 1, whereincontrolled pressure differences are provided between the inlet and the outlet of each of containers in which the samples are fed in parallel.

4. A device for assessing the clogging risks of a well or bore hole passing through a formation, particularly a geological formation, having a fluid flowing therethrough, comprising a plurality of test tubes adapted for containing samples representative of the formation, means for maintaining the whole of said test tubes at substantially the same temperature, means for supplying the test tubes in parallel with controlled amounts of said fluid and means for determining the permeability of the samples as a function of time.

5. The device as claimed in claim 4, wherein at least one of said test tubes is a sample holder comprising a flexible sealed sheath closed at both ends, further comprising means for placing the sample holder under the pressure conditions which reign in the natural site of the sample within said sample holder.

* * * * *